United States Patent [19]

Pinkerton

[11] Patent Number: 5,095,132
[45] Date of Patent: Mar. 10, 1992

[54] USE OF SURFACTANTS IN PHENOL SULFONATE DEHYDRATION

[75] Inventor: Robert B. Pinkerton, Newark, Del.

[73] Assignee: E. I. du Pont de Nemours and Company, Wilmington, Del.

[21] Appl. No.: 617,742

[22] Filed: Nov. 26, 1990

[51] Int. Cl.$^5$ .................. C07C 303/44; C07C 309/42; C07C 303/02; C07C 303/32
[52] U.S. Cl. ..................................... 558/56; 562/124; 562/115; 562/74
[58] Field of Search ................... 562/124, 115, 74; 558/62, 56

[56] References Cited

U.S. PATENT DOCUMENTS

| | | | |
|---|---|---|---|
| 4,486,327 | 12/1984 | Murphy et al. | 252/94 |
| 4,606,838 | 8/1986 | Burns | 252/94 |
| 4,666,636 | 5/1987 | Shen | 260/512 |
| 4,704,236 | 11/1987 | Sankey et al. | 260/402 |

FOREIGN PATENT DOCUMENTS 0294073 12/1988 European Pat. Off. ............. 143/46

OTHER PUBLICATIONS

"The Effect of Surface Active Agents on Crystal Growth Rate and Crystal Habit", Journal of Physical Chemistry, vol. 64, 1960, pp. 13–19.

"The Influence of Surfactants on the Crystallization of L-Isoleucine", Ind. Eng. Chem. Res., vol. 28, No. 3 (1989), pp. 334–340.

Jancic and Grootscholten, *Industrial Crystallization*, pp. 125–130 (1984).

Primary Examiner—Jose G. Dees

[57] ABSTRACT

A process for dehydrating phenol sulfonate salts by azeotropic distillation of water wherein a surfactant such as sodium dodecylbenzene sulfonate is used to prevent the salts from agglomerating and plating out on the walls of the reaction vessel.

16 Claims, No Drawings

USE OF SURFACTANTS IN PHENOL SULFONATE DEHYDRATION

FIELD OF THE INVENTION

This invention relates to a process for the preparation of uniform anhydrous slurries of alkali metal salts or disalts of phenol sulfonic acid.

BACKGROUND OF THE INVENTION

The alkali metal salts and disalts of phenol sulfonic acid are widely used as intermediates in the synthesis of phenol sulfonate esters. These esters, which are useful as bleach activators, can be prepared from salts and disalts of phenol sulfonic acid by reaction with acid chlorides or acid anhydrides.

These alkali metal salts and disalts of phenol sulfonic acid are most readily prepared in aqueous solution by neutralization of phenol sulfonic acid with an appropriate amount of an inorganic base, but must be isolated and dried prior to reaction with acid chlorides or anhydrides in order to avoid excessive yield losses due to hydrolysis of the acid chlorides or anhydrides to their corresponding acids.

In conventional methods for preparing anhydrous alkali metal salts or disalts of phenol sulfonic acid, also known as phenol sulfonate salts, the salt or disalt is isolated as a solid from an aqueous solution either by crystallization or by evaporation of the bulk of the water. The isolated salts are not anhydrous and further drying is required to obtain a substantially water free product. The final drying may be accomplished using conventional methods such as oven drying or azeotropic distillation. By way of example: U.S. Pat. No. 4,666,636 teaches drying sodium phenol sulfonate dihydrate crystals by heating in an inert atmosphere at a temperature between about 140° C. and 200° C. to produce anhydrous sodium phenol sulfonate; U.S. Pat. No. 4,704,236 teaches drying sodium phenol sulfonate dihydrate "by heating it when dispersed in a high boiling aliphatic or aromatic hydrocarbon solvent such that water and solvent are co-removed"; and U.S. Pat. No. 4,486,327 teaches drying disodium phenol sulfonate in a vacuum oven at 115°-120° C.

As may be seen from the above discussion, conventional procedures for the preparation of anhydrous phenol sulfonate salts can be tedious and require a considerable amount of solids handling. This is further complicated by the fact that these salts and disalts tend to be hygroscopic. As a result, the anhydrous salts need to be protected from atmospheric moisture while in storage and during handling.

It has been attempted in the prior art to avoid the need for isolation in the drying of alkali metal salts of phenol sulfonic acid by azeotropic removal of water from aqueous sodium phenol sulfonate. However, azeotropic dehydration of an aqueous sodium phenol sulfonate is complicated by agglomeration of the salt during the drying process. As the water is removed from the aqueous solution, the salt forms lumps in the reaction vessel and plates out on, or sticks to, the vessel walls. This agglomeration is undesirable because it makes the salts difficult to work with on a large scale and results in inefficient dehydration.

This problem is recognized in the art and is discussed in European Pat. Application 0 294 073, which states on Page 3, at lines 12-15:

" . . . we have found that the dehydration of sodium phenol sulfonate by azeotropy on a bulk scale poses tremendous difficulties in that the product tends to agglomerate and fuse together to form large lumps. These lumps interfere with the subsequent esterification, impairing not only the quality of the product, but also the yield."

SUMMARY OF THE INVENTION

The present invention pertains to the direct production of dry crystals or anhydrous slurries of alkali metal salts or disalts of phenol sulfonic acid from aqueous solutions or aqueous slurries containing these salts or disalts without the need for an intermediate isolation of a phenol sulfonic acid alkali metal salt in an nonanhydrous form.

The present invention eliminates the problems associated with azeotropic drying, such as agglomeration, by including an effective amount of an appropriate surfactant in a distillation mixture of an aqueous alkali metal phenol sulfonate salt or disalt and an organic solvent.

This invention applies to alkali metal salts and disalts of phenol sulfonic acid, although sodium salts are preferred because they are the most practical and economical salts. Use of the more soluble potassium salts and still more soluble lithium salts is more limited than the use of the sodium salts because as the solubility of the salts increases, the tendency of the distillation mixture to foam during azeotropy increases.

DETAILED DESCRIPTION OF THE INVENTION

The present invention is based on the discovery that aqueous alkali metal salts of phenol sulfonic acid may be efficiently dehydrated by azeotropic distillation using a hydrocarbon solvent by adding an appropriate type and amount of a surfactant to the distillation mixture prior to dehydration. The inventive process produces a uniform anhydrous slurry of the salt. When a surfactant is not used in the azeotropic dehydration process, a very non-uniform, agglomerated, caked intractable mass of the salt results.

The process of this invention may be used to dehydrate hydrated forms of alkali metal salts and disalts of phenol sulfonic acid, as well as aqeous solutions and slurries of these salts. For example, this invention may be used to dehydrate commercial sodium phenol sulfonate (SPS) dihydrate as well as aqueous solutions of SPS that are prepared by neutralizing phenolsulfonic acid.

The hydrocarbon solvent may be an aliphatic or aromatic solvent such as toluene, xylene, hexane, heptane, octane, nonane, decane or mixtures thereof.

The choice of an appropriate surfactant, as described below, is empirical because of the many variables in the process, such as the concentration of the surfactant and the type and amount of organic solvent.

In general, there is a "window" of surfactant concentration in which these salts are successfully dehydrated while at the same time avoiding a foam over. Too little as well as too much of a particular surfactant may cause excessive foaming, which would classify that particular experiment as a failure. Each surfactant type that functions successfully in this invention is a unique case. The "window" of activity depends upon the solubility of the alkali metal salt of the sulfonate, its aqueous concentration, the specific structure of the surfactant and the amount and type of the azeotropy solvent.

The process of this invention may be practiced using anionic, nonionic, amphoteric or cationic surfactants. Anionic surfactants are preferred because they provide useful performance over a wide range of concentrations. Alkylbenzenesulfonates are particularly useful anionic surfactants in the process of this invention, an example of which includes sodium dodecyl benzene sulfonate.

When anionic surfactants are employed, the surfactant may be introduced in its neutralized form or by adding the corresponding free acid to the aqueous phenol sulfonic acid prior to or during the neutralization of the phenol sulfonic acid.

The inventive process is especially well suited for reaction sequences involving subsequent reaction with an acid halide to produce a phenol sulfonate ester because the process of this invention produces alkali metal salts and disalts that are sufficiently anhydrous and finely divided that they may be converted directly to phenol sulfonate esters. Accordingly, there is no need to isolate the intermediate phenol sulfonate and the entire process of preparing a bleach activator may take place in a single reactor or series of reactors.

Phenol sulfonic acid may be prepared by methods known in the art, such as by sulfonating phenol by adding sulfuric acid to phenol, or it may be obtained commercially as an aqueous solution. Aqueous phenol sulfonic acid may be converted to its mono and dialkali metal salts by neutralization of the acid with alkali metal hydroxides, alkali metal carbonates or alkali metal bicarbonates using conventional methods.

The resulting aqueous mixtures of the salts may then be dehydrated by adding between 0.08 to 13.7 wt %, based on the expected theoretical weight of the anhydrous sodium phenol sulfonate, of an appropriate surfactant and an appropriate volume of an aliphatic or aromatic hydrocarbon solvent. This distillation mixture of an aqueous salt, a surfactant, and an organic solvent is then heated with azeotropic removal of the water until no more water is collected.

The amount of hydrocarbon solvent is not critical, so long as enough solvent is used so that the distillation mixture remains mobile during dehydration. Typically, between 0.3 and 1.5 l of solvent is required per mole of salt or disalt of phenol sulfonic acid, although even larger volumes of solvent may be beneficially employed. An insufficient amount of solvent causes the phenol sulfonate salt slurry to become too thick as it dehydrates, which in turn causes an increase in the tendency of the mixture to foam during the last stages of the dehydration, viz., as the temperature of the mixture increases from the water/azeotrope boiling point to the boiling point of the pure organic solvent. More specifically, in the case of mixed xylenes, the temperature range of 100° C. to 140° C. was critical because in this temperature range, the mixture began to foam.

The inventive method of dehydration produces a finely divided anhydrous white to cream colored slurry of the phenol sulfonate salt which may be readily isolated from the organic solvent by conventional methods, such as filtration or evaporation of the solvent. Alternately the anhydrous slurry may be esterified in situ using an acid chloride to produce a slurry of an acylphenol sulfonate bleach activator.

This inventive process of dehydrating an aqueous solution of a phenol sulfonate salt is much preferred to conventional methods of dehydration because, in contrast to conventional methods, it does not require that the salt first be isolated in a nonanhydrous form and then further dried to give anhydrous material.

EXAMPLE 1

Disodium phenol sulfonate (DSPS) was prepared from commercial sodium phenol sulfonate (SPS) dihydrate (Eastman Kodak, Rochester, N.Y.) as follows.

First it was attempted to make DSPS from SPS using a conventional method. 232 g of commercial SPS dihydrate (1 mole) was dissolved in 450 ml water and 146 g (1.1 mole) 30% sodium hydroxide solution was added. When all the SPS was dissolved, 1 liter of mixed xylene was added and the mixture refluxed with water removal through a Dean-Stark trap. As the water was removed, solid DSPS began to agglomerate and stick to the walls of the flask and to the thermometer. The experiment was stopped and the water returned to the flask to dissolve the solids.

Next, DSPS was prepared from SPS dihydrate using the inventive process. 4.0 g of sodium dodecylbenzene sulfonate surfactant (1.7% of Wt of SPS) was added to the flask containing SPS, water, and sodium hydroxide, and the mixture was refluxed with water removal through the Dean-Stark trap as above. As the water was removed, solid DSPS separated out to give a finely divided slurry and did not stick to the walls of the flask.

When the above experiment was repeated, using the surfactant, a homogeneous white to slightly tan slurry of the product was obtained and no caking, agglomeration or sticking to the walls of the flask was observed. After six hours, no further water was observed to be coming off. A sample of the slurry was withdrawn and analyzed at 0.4 wt % water via Karl Fisher water analysis.

This experiment was repeated using one half the amount of sodium dodecylbenzene sulfonate surfactant (0.84%), and produced similar results, yielding 218 g of dry DSPS versus the theoretical yield of 222 g. The DSPS analyzed at 0.37 wt % water.

EXAMPLE 2

Sodium chloroacetylphenol sulfonate, an intermediate for a bleach activator, was made by sulfonating phenol as follows.

188 g (2.0 moles) of phenol (J. T. Baker, Phillipsburg, N.J.) was added to 208 g (2.1 moles) of 96-98% sulfuric acid, and the mass held at 100°-105° C. for 5 hours, which produced an orange/red sulfonation mass of phenol sulfonic acid. 800 cc of water was added to the mass, followed by 539 g of 30% sodium hydroxide to produce an aqueous phenol sulfonate salt having a pH of 10. Then 4.0 g sodium dodecylbenzene sulfonate surfactant was added, followed by 1.0 liter of mixed xylenes, and the mass was refluxed overnight. The total amount of water removed was 1250 cc and the moisture content of the fine, uniform slurry at that point was 0.4 wt %. This slurry was then treated directly with 237 g (2.09 moles) of chloroacetyl chloride (Aldrich, Milwaukee, Wis.) in refluxing xylene for two additional hours. The product was filtered and pan dried to give a mixture of 616.6 g of sodium chloroacetylphenol sulfonate, sodium chloride, and surfactant versus a theoretical yield of 670.0 g.

This product may then be treated with a sodium alkanoate, such as is disclosed in U.S. patent application Ser. No. 07/359,981, filed June 6, 1989, now U.S. Pat.

No. 4,985,180 and assigned to E. I. du Pont de Nemours and Company, the text of which is incorporated by reference, to produce a bleach activator.

EXAMPLE 3

Sodium Nonyloxybenzene Sulfonate, a bleach activator, was produced from sodium phenol sulfonate dihydrate as follows.

116 g SPS dihydrate was dissolved in 300 cc water along with 0.4 g sodium dodecylbenzene sulfonate surfactant. 300 cc of xylene was added and the mass was refluxed to a point where the SPS contained 0.33 wt % water. 200 g more of xylene was added to the mass to replace some of the water removed. 92.4 cc of pelargonoyl chloride (Aldrich, Milwaukee, Wis.) was added over a period of 25 min. at the reflux temperature (140° C.). The reaction mass was held at reflux for three hours, filtered hot, and washed two times with 200 cc of xylene to produce, upon drying, 155.3 g of the bleach activator. The bleach activator was analyzed by liquid chromatography and found to be 92 wt % sodium nonyloxybenzene sulfonate, or 85% of the theoretical yield.

EXAMPLES 4-29

SPS (sodium p-hydroxybenzenesulfonate dihydrate) (Eastman Kodak Company, Rochester, N.Y.) was azeotropically dehydrated using various surfactants, and the results of those experiments are summarized below in Table 1.

The surfactant levels for all the experiments are given as wt % based on the SPS dihydrate charged. The same procedure was followed in all the experiments:

a. 58 g of SPS dihydrate was dissolved in 150 cc deionized water.
b. surfactant was added to the SPS/water mixture.
c. The pH was then checked to be sure it was in the range of 5.0-5.5. If the pH was outside this range, it was adjusted with a few drops of sodium hydroxide.
d. 300 cc mixed xylenes were added and the mixture was azeotropically dehydrated using a Dean Stark trap.

Observations were then made as to general foam levels throughout the dehydration process as it progressed from an initial temperature of 100° C. through 110° C. and on up to 140° C., when all the water had been removed. The temperature range of 100° C. through 110°-115° C. always appeared to be critical, as that was when dehydration activity was maximized, and was when the greatest tendency to foam was evident. Each example was rated a success if it could be completed to 140° C. without foaming and if the resulting slurry was uniform with no agglomeration of the salt.

Under the "RESULTS/COMMENTS" section in the table below, it will be noted as to whether the particular surfactant passed or failed in performance. Also, the numbers written in this column correspond to the key below:

1 = best results
2 = no foam, looked good
3 = low foam,
4 = high foam
5 = some SPS stuck to vessel walls
6 = borderline pass due to foaming and/or SPS sticking to vessel walls
7 = foamed over (failed)
8 = excessive SPS sticking to vessel walls (failed)
9 = product SPS was coarse and sandy In Examples 4-27, pure commercial sodium phenol sulfonate dihydrate was used instead of generating the sodium phenol sulfonate dihydrate each time from phenol and sulfuric acid. In other experiments, it was shown that SPS generated from phenol, sulfuric acid, and sodium hydroxide, worked in the same manner.

In Sections F and G, which includes Examples 28 and 29, other phenolate salts, namely, potassium and lithium, were used. These were generated by neutralizing commercial 4-hydroxybenzene sulfonic acid (Aldrich, Milwaukee, Wis.) with an appropriate alkali metal hydroxide.

TABLE 1

| | SURFACTANT | WT % | RESULT/COMMENTS |
|---|---|---|---|
| A. | ANIONIC SURFACTANTS | | |
| 4. | sodium dodecylbenzene sulfonate[a] | 0.05-2.58 | Pass, 1 |
| | | 4.30-13.70 | Pass, 3 |
| 5. | Biosoft 130-S[b] (mixture of linear alkyl benzene sulfonic acid-free acid form) | 0.43-1.29 | Fail, 7 |
| | | 2.40-3.10 | Pass, 3 |
| | | 3.45-6.89 | Pass, 4 |
| 6. | Avitone A Softner[c] (mixture of parafinic long chain sodium alkyl sulfonates) | 0.017-0.086 | Fail, 7 |
| | | 0.18-1.68 | Pass, 2 |
| | | 3.44 | Fail, 7 |
| 7. | Alkanol XC[d] (alkylaryl sulfonate) | 0.15 | Fail, 7 |
| | | 0.08 | Pass, 6 |
| | | 0.17-02.58 | Pass, 2 |
| | | 4.3 | Fail, 7 |
| | | 5.20-06.89 | Pass, 6 |
| 8. | DuPonol ME[e] (Cl2 alcohol sulfate) | 0.086-0.43 | Pass, 9 |
| | | 0.86 | Pass, 5 |
| B. | NONIONIC SURFACTANTS | | |
| 9. | Alkanol ACN[f] (aliphatic amine ethoxylate in isobutyl alcohol and water) | 0.086-0.17 | Fail, 7 |
| 10. | Igepal 530[g] [nonylphenoxypoly-(ethyleneoxy)ethanol] | 0.086-01.72 | Fail, 8 |
| 11. | Tween 80[h] [PIE (20) sorbitan monooleate] | 0.086-0.34 | Fail, 7 |
| 12. | Merpol A[i] (alcohol EO condensate) | 0.086-0.34 | Pass, 5 |
| 13. | Merpol SE[j] (alcohol EO condensate) | 0.51-03.40 | Fail, 7 |
| C. | AMPHOTERIC SURFACTANTS | | |
| 14. | Retarder LAN[k] (cetyllauryltrimethyl ammonium bromide is active ingredient) | 0.086-0.86 | Pass, 6 |
| | | 1.70-13.70 | Fail, 7 |
| 15. | Product BCO[l] (C-alkyl betaine) | 0.086-1.70 | Fail, 7 |
| D. | CATIONIC SURFACTANTS | | |
| 16. | Arquad 1250[m] (N-dodecyl trimethylammonium chloride, 50%) | 0.17 | Fail, 4,5,9 |
| 17. | Arquad 1850[n] (N-octadecyl trimethylammonium chloride, 50%) | 0.17-0.43 | Pass, 4 |
| | | 1.72 | Fail, 7 |
| 18. | Avitex NA[o] (quaternized amine condensate) | 0.086 | Pass, 5 |
| | | 0.17-0.34 | Fail, 7 |
| 19. | Duoquad T-50[p] (diquaternary ammonium chloride, 50%) | 0.086-0.34 | Fail, 7 |
| 20. | Arquad 2-C-75[q] | 0.086-1.70 | Pass, 3 |

TABLE 1-continued

| SURFACTANT | WT % | RESULT/ COMMENTS |
|---|---|---|
| (dimethyldicocoammonium chloride, 75% active) | | |
| 21. Aliquat 336[r] (methyl trialkylammonium chloride) | 0.086–1.72 | Fail, 8 |
| 23. Arquad 16-29[s] (trimethylhexadecylammonium chloride) | 0.086 / 0.86–1.72 | Pass, 6 / Fail, 7 |
| 24. Duoquad T-50[t] (diquaternary ammonium chloride, 50%) | 0.086–1.72 | Fail, 7 |
| E. FLUOROSURFACTANTS | | |
| 25. ZONYL TBS[u] (perfluoroalkyl sulfonic acid) | 0.086–0.34 | Fail, 8 |
| 26. Zonyl FSA[v] (perfluoroalkyl sulfonic acid) | 0.086–0.51 | Fail, 7, 8 |
| 27. Zonyl FSC[w] | 0.17–1.03 | Fail, 7, 8 |
| F. POTASSIUM PHENOLSULFONATE | | |
| 28. sodium dodecyl benzene sulfonate[x] | 0.25 / 2.50 | Fail 7 / Pass 2 |
| G. LITHIUM PHENOL SULFONATE | | |
| 29. sodium dodecyl benzene sulfonate | 0.50–5.20 | Fail 4, 7 foam over only, no agglomeration |

[a]Tennessee Chemical, Atlanta, GA
[b]Stepan Co., Northfield, IL
[c]Du Pont Company, Wilmington, DE
[d]Du Pont Company, Wilmington, DE
[e]Du Pont Company, Wilmington, DE
[f]Du Pont Company, Wilmington, DE
[g]Rhone-Poulenc/GAF, Monmouth Junction, NJ
[h]ICI, Wilmington, DE
[i]Du Pont Company, Wilmington, DE
[j]Du Pont Company, Wilmington, DE
[k]Du Pont Company, Wilmington, DE
[l]Du Pont Company, Wilmington, DE
[m]Akzo Chemicals, Inc., New Brunswick, NJ
[n]Akzo Chemicals, Inc., New Brunswick, NJ
[o]Du Pont Company, Wilmington, DE
[p]Akzo Chemicals, Inc., New Brunswick, NJ
[q]Akzo Chemicals, Inc., New Brunswick, NJ
[r]Henderson Company
[s]Akzo Chemicals, Inc., New Brunswick, NJ
[t]Akzo Chemicals, Inc., New Brunswick, NJ
[u]Du Pont Company, Wilmington, DE
[v]Du Pont Company, Wilmington, DE
[w]Du Pont Company, Wilmington, DE
[x]Tennessee Chemical, Atlanta, GA

I claim:

1. A process for the preparation of a phenol sulfonate ester wherein an aqueous solution of an alkali metal salt or disalt of phenol sulfonic acid is mixed with an aliphatic or aromatic hydrocarbon solvent to form a distillation mixture, the distillation mixture is dehydrated by azeotropically distilling water from the distillation mixture to produce a slurry of an alkali metal phenol sulfonic salt or disalt, and esterifying the slurry of the alkali metal phenol sulfonic salt or disalt to form an acylphenol sulfonate, the improvement which comprises:

adding an effective amount of a surfactant to the distillation mixture so that the dehydration of the distillation mixture by azeotropic distillation produces a uniform anhydrous slurry of an alkali metal phenol sulfonic salt or disalt.

2. The process of claim 1, wherein the anhydrous slurry of the alkali metal phenol sulfonic salt or disalt is esterified using an acid chloride.

3. A process for the preparation of a uniform anhydrous slurry of an alkali metal salt or disalt of phenol sulfonic acid wherein an aqueous solution of an alkali metal salt or disalt of phenol sulfonic acid is mixed with an aliphatic or aromatic hydrocarbon solvent to form a distillation mixture and the distillation mixture is dehydrated by azeotropically distilling water from the distillation mixture, the improvement which comprises:

adding an effective amount of a surfactant to the distillation mixture so that the dehydration of the distillation mixture by azeotropic distillation produces a uniform anhydrous slurry of an alkali metal phenol sulfonic salt or disalt.

4. The process of claim 3 including the step of removing the organic solvent from the anhydrous slurry of the alkali metal phenol sulfonic salt or disalt to produce dry crystals of the alkali metal phenol sulfonic salt or disalt.

5. The process of claim 3 wherein the surfactant is an anionic surfactant, a nonionic surfactant, an amphoteric surfactant or a cationic surfactant.

6. The process of claim 5, wherein the salt or disalt of the phenol sulfonic acid is a potassium or sodium phenol sulfonate salt or disalt.

7. The process of claim 3 wherein the salt is a potassium phenol sulfonate salt or disalt.

8. The process of claim 5, wherein the surfactant is anionic.

9. The process of claim 8, wherein the anionic surfactant is sodium dodecylbenzene sulfonate.

10. The process of claim 9, wherein the sodium dodecylbenzene sulfonate is about 2.5 wt % of the potassium phenol sulfonate salt or disalt.

11. The process of claim 3, wherein the salt is a sodium phenol sulfonate salt or disalt.

12. The process of claim 11, wherein the surfactant is anionic.

13. The process of claim 12 wherein the anionic surfactant is sodium dodecylbenzene sulfonate.

14. The process of claim 13 wherein the sodium dodecylbenzene sulfonate is from 0.05 to 13.70 wt. % of the sodium phenol sulfonate salt or disalt.

15. The process of claim 14 wherein the sodium dodecylbenzene sulfonate is from 0.05 to 2.58 wt % of the sodium phenol sulfonate salt or disalt.

16. A process for preparation of a uniform anhydrous slurry of an alkali metal salt or disalt of phenol sulfonic acid wherein a dihydrate form of an alkali metal salt or disalt of phenol sulfonic acid is mixed with an aliphatic or aromatic hydrocarbon solvent to form a distillation mixture and the distillation mixture is dehydrated by azeotropically distilling water from the distillation mixture, the improvement which comprises:

adding an effective amount of a surfactant to the distillation mixture so that the dehydration of the distillation mixture by azeotropic distillation produces a uniform anhydrous slurry of an alkali metal phenol sulfonic salt or disalt.

* * * * *